(12) United States Patent
Makino et al.

(10) Patent No.: US 9,395,298 B2
(45) Date of Patent: Jul. 19, 2016

(54) BLOOD COAGULATION ANALYZER

(75) Inventors: Akihisa Makino, Hitachinaka (JP);
Tomonori Mimura, Kasama (JP);
Terumi Tamura, Hitachinaka (JP);
Sakuichiro Adachi, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 363 days.

(21) Appl. No.: 13/509,661

(22) PCT Filed: Nov. 19, 2010

(86) PCT No.: PCT/JP2010/070741
§ 371 (c)(1),
(2), (4) Date: Jul. 6, 2012

(87) PCT Pub. No.: WO2011/068049
PCT Pub. Date: Jun. 9, 2011

(65) Prior Publication Data
US 2012/0282139 A1    Nov. 8, 2012

(30) Foreign Application Priority Data
Dec. 4, 2009    (JP) .................................. 2009-276229

(51) Int. Cl.
*G01N 33/50* (2006.01)
*G01N 21/00* (2006.01)
(Continued)

(52) U.S. Cl.
CPC .............. *G01N 21/51* (2013.01); *G01N 21/532* (2013.01); *G01N 33/1826* (2013.01); *G01N 33/4905* (2013.01); *G01N 33/86* (2013.01); *G01N 33/18* (2013.01); *G01N 2021/825* (2013.01)

(58) Field of Classification Search
CPC . G01N 21/51; G01N 21/532; G01N 33/4905; G01N 33/86; G01N 33/18; G01N 33/1826; G01N 2021/825
See application file for complete search history.

(56) References Cited

U.S. PATENT DOCUMENTS 4,577,963 A * 3/1986 Traina .................... G01N 15/06
356/28.5
(Continued)

FOREIGN PATENT DOCUMENTS

| EP | 1 840 559 A1 | 10/2007 |
| JP | 58-172537 A | 10/1983 |

(Continued)

OTHER PUBLICATIONS

Kalchenko, Vyacheslav, et al. "In vivo dynamic light scattering imaging of blood coagulation." Journal of biomedical optics 12.5 (2007): 052002-052002.*

(Continued)

*Primary Examiner* — Lyle Alexander
*Assistant Examiner* — Robert Eom
(74) *Attorney, Agent, or Firm* — Mattingly & Malur, PC

(57) ABSTRACT

A blood coagulation analyzer that realizes both securement of a wide dynamic range and enhancement of sensitivity in blood coagulation analysis by selecting an appropriate angle of detection depending on the intensity of scattered light from each specimen without causing complexity of the analyzer. The analyzer has a reaction container. A storage unit is provided which takes in and stores multiple pieces of chronological light intensity variation data acquired from detectors arranged around a reaction container. A judgment unit selects light intensity variation data to be used for calculation of a blood coagulation time from the multiple pieces of light intensity variation data stored in the storage unit based on the amount of light intensity variation. A calculation unit calculates the blood coagulation time from the light intensity variation data selected by the judgment unit.

6 Claims, 5 Drawing Sheets

(51) Int. Cl.
*G01N 21/51* (2006.01)
*G01N 33/49* (2006.01)
*G01N 33/86* (2006.01)
*G01N 21/53* (2006.01)
G01N 21/82 (2006.01)
G01N 33/18 (2006.01)

(56) References Cited

U.S. PATENT DOCUMENTS

| | | | |
|---|---|---|---|
| 4,755,058 A | 7/1988 | Shaffer | |
| 4,766,083 A | 8/1988 | Miyashita et al. | |
| 2003/0058450 A1* | 3/2003 | Mosley | G01N 21/3151 356/436 |
| 2007/0248490 A1 | 10/2007 | Matsuo et al. | |
| 2009/0185160 A1 | 7/2009 | Mantele et al. | |

FOREIGN PATENT DOCUMENTS

| | | |
|---|---|---|
| JP | 61-13136 A | 1/1986 |
| JP | 06-249855 A | 9/1994 |
| JP | 2004-020542 A | 1/2004 |
| JP | 2007-263912 A | 10/2007 |

OTHER PUBLICATIONS

Chinese Office Action received in Chinese Application No. 201080054740.3 dated Jul. 3, 2014.

Japanese Office Action received in corresponding Japanese Application No. 2014-253019 dated Dec. 1, 2015.

* cited by examiner

BLOOD COAGULATION ANALYZER

TECHNICAL FIELD

The present invention relates to a blood coagulation analyzer which measures the coagulation time of blood by use of optical means by mixing blood plasma with a blood coagulation reagent and thereby causing precipitation of fibrin.

BACKGROUND ART

Blood flows inside the blood vessels while keeping its fluidity. However, once the bleeding occurs, coagulation factors existing in the blood plasma and in the blood platelets are activated in a chain reaction. Fibrinogen contained in the blood plasma is transformed into fibrin and the precipitation of the fibrin leads to the hemostasis.

Such blood coagulability includes endogenous coagulability which stops the bleeding within a tissue and exogenous coagulability which stops the bleeding caused by an external injury, etc. Measurement items regarding the blood coagulability include the prothrombin time (PT) as an exogenous blood coagulation reaction test, the activated partial thromboplastin time (APTT) as an endogenous blood coagulation reaction test, the fibrinogen level (Fbg), etc. All these items are measured by detecting the precipitation of fibrin, caused by adding a reagent for starting the blood coagulation, by an optical, physical or electrical technique.

In a known method employing optical means, the time in which fibrin starts precipitating is calculated by irradiating the reaction solution with light and detecting the precipitation of the fibrin in the reaction solution as chronological intensity variation of scattered light or transmitted light.

When such an optical technique is used, effects of interfering substances (hemoglobin, bilirubin, chyle, etc.) in the sample are nonnegligible. Therefore, a lot of efforts have been made to figure out the way to eliminate the effects of the interfering substances. In a technique described in Patent Literature 1, for example, the reaction solution is irradiated with multiple-wavelength light. Data corresponding to a wavelength at which the effects of the interfering substances are weak is selected depending on the specimen (target of the measurement) and the selected data is used for the calculation of the coagulation time.

In a technique described in Patent Literature 2, a plurality of light scattering intensities are measured at different angles with respect to the optical axis of a single laser light source.

PRIOR ART LITERATURE

Patent Literature

Patent Literature 1: JP-2007-263912-A
Patent Literature 2: JP-58-172537-A

SUMMARY OF THE INVENTION

Problem to be Solved by the Invention

In the technique described in the Patent Literature 1, it is difficult to construct a simple and highly reliable device at a low manufacturing cost since the mechanism is necessitated to be complex for the preparation of the multiple-wavelength light.

Meanwhile, in the technique described in the Patent Literature 2, each detector is optimized for blood coagulation analysis or antigen-antibody reaction analysis using a latex reagent, etc. The patent literature focuses on the implementation of the blood coagulation analysis and the antigen-antibody reaction measurement by one device and refers to no further effects.

It is also possible, as a technique for realizing both securement of a wide dynamic range and enhancement of the sensitivity in the blood coagulation analysis, to switch the amplification factor (gain) depending on the amount of light detected in the initial stage of the measurement. However, in the coagulation time measurement employing optical detection, making the judgment on the switching in the initial stage of the measurement is practically impossible since the coagulability can vary widely from specimen to specimen (even when the amount of the scattered light in the initial stage is large due to chyle, etc.) and there are also cases (e.g., abnormal specimen) where the measurement draws a coagulation curve like a two-stage reaction.

Furthermore, while it is also possible to simultaneously acquire data with multiple amplification factors (gains) and select the light intensity variation data to be used for the analysis after the completion of the reaction, just changing the amplification factor cannot also control the measurement sensitivity. Thus, such a technique is totally different from the technique of the present invention in which light intensity variation data at two angles differing in the sensitivity are acquired simultaneously.

The object of the present invention, which has been made in consideration of the above problems, is to provide a blood coagulation analyzer that realizes both the securement of a wide dynamic range and the enhancement of the sensitivity in the blood coagulation analysis by selecting an appropriate angle of detection depending on the intensity of the scattered light from each specimen, without causing the complexity of the device (analyzer).

Means for Solving the Problem

The configuration of the present invention for achieving the above object is as follows:

A blood coagulation analyzer comprising: a reaction container for allowing a sample and a reagent to mix and react with each other; a light source for irradiating the reaction container with light; a plurality of detectors arranged around the reaction container at different angles with respect to an optical axis of the light source for detecting scattered light emitted from the liquid mixture of the sample and the reagent; a storage unit which takes in and stores multiple pieces of chronological light intensity variation data acquired from the detectors; a judgment unit which selects light intensity variation data to be used for calculation of a blood coagulation time from the multiple pieces of light intensity variation data stored in the storage unit based on the amount of light intensity variation; and a calculation unit which calculates the blood coagulation time from the light intensity variation data selected by the judgment unit.

Effect of the Invention

The present invention makes it possible to provide a blood coagulation analyzer capable of securing a wide dynamic range of the signal detection by mitigating the effects of the interfering substances and the difference in the blood coagulability among specimens while also realizing high-sensitivity and highly-reproducible analysis with high signal levels even for specimens yielding low-level signals.

MODE FOR CARRYING OUT THE INVENTION

Figure 1:
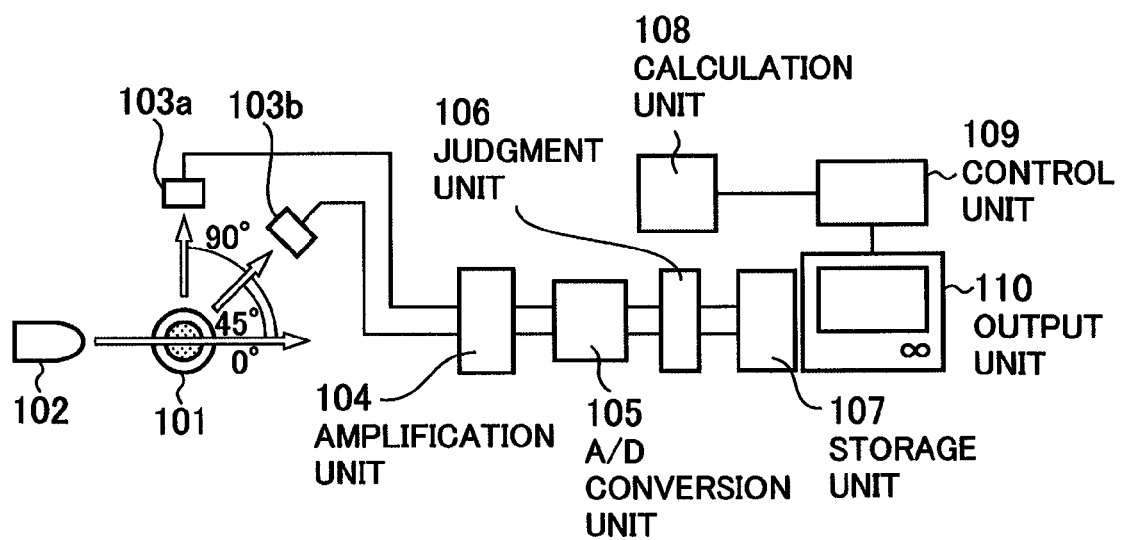
FIG. 1 is a schematic block diagram showing the overall configuration of a blood coagulation analyzer in accordance with the present invention.

Referring now to the drawings, a description will be given in detail of preferred embodiments in accordance with the present invention.

FIG. 1 shows the overall configuration of a blood coagulation analyzer which embodies the present invention. A sample is dispensed by a sample dispensing mechanism not shown into an optically transparent reaction container 101. Thereafter, a reagent is dispensed by a reagent dispensing mechanism not shown into the reaction container 101.

The liquid mixture of the sample and the reagent in the reaction container 101 is irradiated with light emitted by a single-wavelength light source 102 (LED, laser, etc.). Scattered light from the liquid mixture is received by a plurality of detectors 103a-103b (photodiodes, phototransistors, etc.) to which priority orders have previously been assigned. In this embodiment, the detectors 103a-103b are arranged on a horizontal plane including the optical axis of the single-wavelength light source 102. A direction coinciding with the optical axis is defined as 0°.

Thus, "45° with respect to the optical axis" means that forward-scattered light in the 45° direction can be detected. The light received by each detector 103a-103b is transduced into photocurrent, amplified by an amplification unit 104, converted from an analog signal into a digital signal by an A/D conversion unit 105, and stored in a storage unit 107 via a judgment unit 106 as chronological light intensity variation data.

By using the stored light intensity variation data from the detectors 103a-103b, the judgment unit 106 judges which light intensity variation data (from the detector 103a or from the detector 103b) should be used for the calculation of the blood coagulation time according to a judgment procedure which will be described later. The selected light intensity variation data is transmitted to a calculation unit 108. The calculation unit 108 calculates the blood coagulation time from the selected light intensity variation data and transmits the result of the calculation to a control unit 109. The control unit 109 outputs the result to an output unit 110.

There are several known methods for calculating the blood coagulation time, such as a method that defines the coagulation time as a time in which the light intensity variation data reaches a prescribed level, a method that differentiates the light intensity variation data and defines the coagulation time as a time in which the derivative of the light intensity variation data changing with time reaches the maximum, and a method that defines the coagulation time as a time corresponding to 1/N of the time in which the derivative of the light intensity variation data reaches the maximum. In these methods, the coagulation time is calculated exclusively by grasping the light intensity variation (variation in the light intensity). Thus, the coagulation time is not directly affected by the absolute value of the light intensity.

Therefore, also in this embodiment, even if the absolute value of the light intensity varies depending on the angle of arrangement, the blood coagulation times obtained in such circumstances can be handled as practically identical data as long as the light intensity variation data has been acquired properly.

Figure 2:
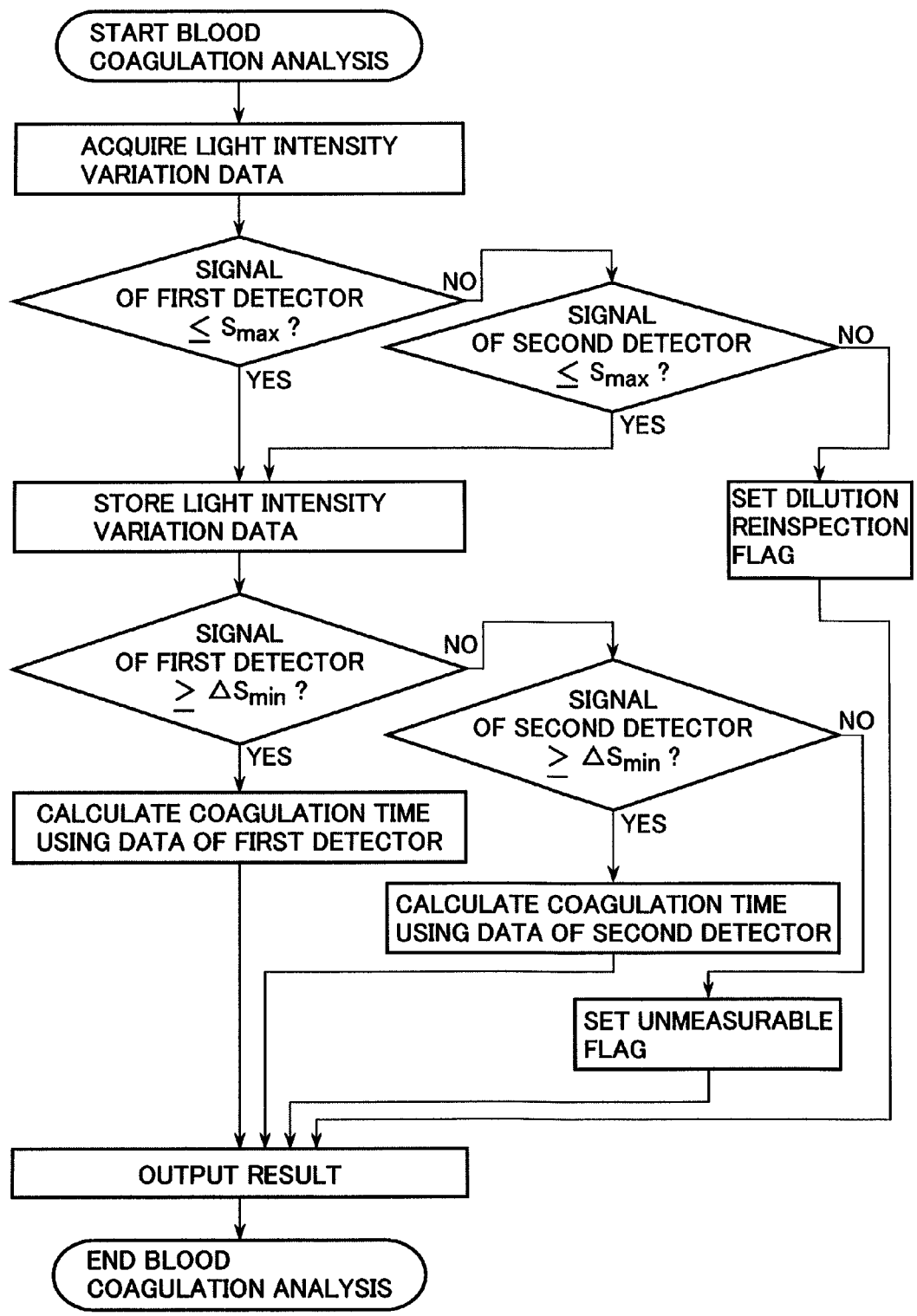
FIG. 2 is a flow chart of blood coagulation analysis in an embodiment of the present invention.

FIG. 2 is a flow chart of blood coagulation analysis in this embodiment. In this embodiment, two detectors 103a and 103b arranged in two directions will be explained. A detector 103a in a 90° direction with respect to the optical axis is set as a first detector of the higher priority order, while a detector 103b in a 45° direction with respect to the optical axis is set as a second detector of the lower priority order. This setting is made based on criteria that the signal from the first detector of the higher priority order should have (1) higher signal stability (lower noise) and (2) lower signal base level (lower reagent blank signal level) compared to the signal from the second detector of the lower priority order.

The reaction container 101 containing the dispensed sample and reagent is irradiated with the light from the single-wavelength light source 102. Scattered light emitted from the liquid mixture of the sample and the reagent is received by the first detector 103a and the second detector 103b, transduced into photocurrents, and sent to the amplification unit 104. The photocurrents are amplified by the amplification unit 104, converted into digital signals by the A/D conversion unit 105, and stored in the storage unit 107 via the judgment unit 106 as scattered light intensity variation data. In this case, the judgment unit 106 carries out the transmission of the data to the storage unit 107 while confirming that the signals from the first and second detectors 103a and 103b are not greater than a preset signal intensity upper limit Smax. When the reaction is saturated after the detection of the start of the fibrin precipitation and the rate of change of the signal from either one of the detectors remained not greater than a preset signal change rate ΔSfin for a preset time period (e.g., 10 seconds), the blood coagulation reaction is judged to have finished and the scattered light measurement is ended. In case where the judgment unit 106 detects that both the signals from the first and second detectors 103a and 103b exceeded the signal intensity upper limit Smax continuously for a preset time period (e.g., 3 seconds) before the end of the measurement, the measurement is ended immediately and a flag for requesting a dilution re-inspection is transmitted to the control unit 109.

When at least one of the signals from the first and second detectors 103a and 103b is less than or equal to the signal intensity upper limit Smax, the measurement is continued until the end of the measurement or until a preset longest measurement time Tlim (e.g., 300 seconds) elapses. After the measurement is ended, the judgment unit 106 checks whether or not the amount of change of the signal of the first detector 103a from a signal base level is a preset minimum signal intensity variation ΔSmin or more. When the signal variation is the minimum signal intensity variation ΔSmin or more, the judgment unit 106 transmits the scattered light intensity variation data corresponding to the first detector 103a to the calculation unit 108 for the calculation of the blood coagulation time. In contrast, when the signal variation of the signal of the first detector 103a is less than or equal to the minimum signal intensity variation ΔSmin, the judgment unit 106 shifts to the check of the signal of the second detector. When the signal variation of the signal of the second detector 103b from the signal base level is the minimum signal intensity variation ΔSmin or more, the judgment unit 106 transmits the scattered light intensity variation data corresponding to the second detector 103b to the calculation unit 108 for the calculation of the blood coagulation time. In contrast, when the signal variation of the signal of the second detector 103b is less than or equal to the minimum signal intensity variation ΔSmin, the judgment unit 106 transmits a flag indicating "unmeasurable" to the control unit 109. The blood coagulation time, the dilution re-inspection request flag and the unmeasurable flag are transmitted from the control unit 109 to the output unit 110 and outputted.

Figure 3:
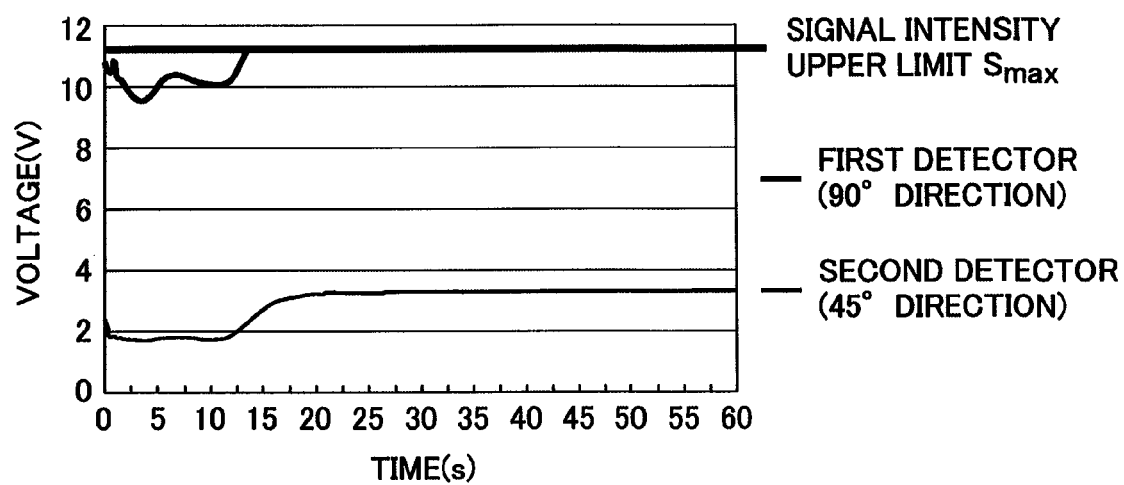
FIG. 3 shows light intensity variation data actually acquired in prothrombin time measurement of a specimen having standard coagulability in an embodiment of the present invention.

FIG. 3 shows the light intensity variation data actually acquired in prothrombin time measurement of a specimen having standard coagulability. FIG. 3 indicates that the signal of the second detector 103b exceeds the signal intensity upper limit Smax whereas the signal of the first detector 103a still has a safety margin against an increase in the signal base level caused by interfering substances such as chyle. By using the signal of the first detector 103a for the measurement, a wide dynamic range of the signal detection can be secured.

Figure 4:
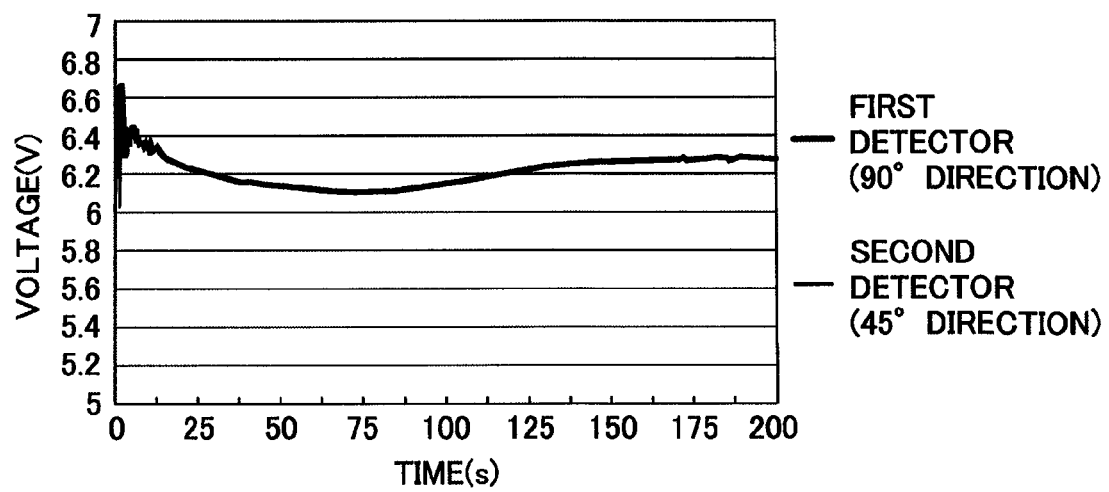
FIG. 4 shows the light intensity variation data actually acquired in the prothrombin time measurement of a sample obtained by diluting 16-fold the specimen having standard coagulability in an embodiment of the present invention.
Figure 4:
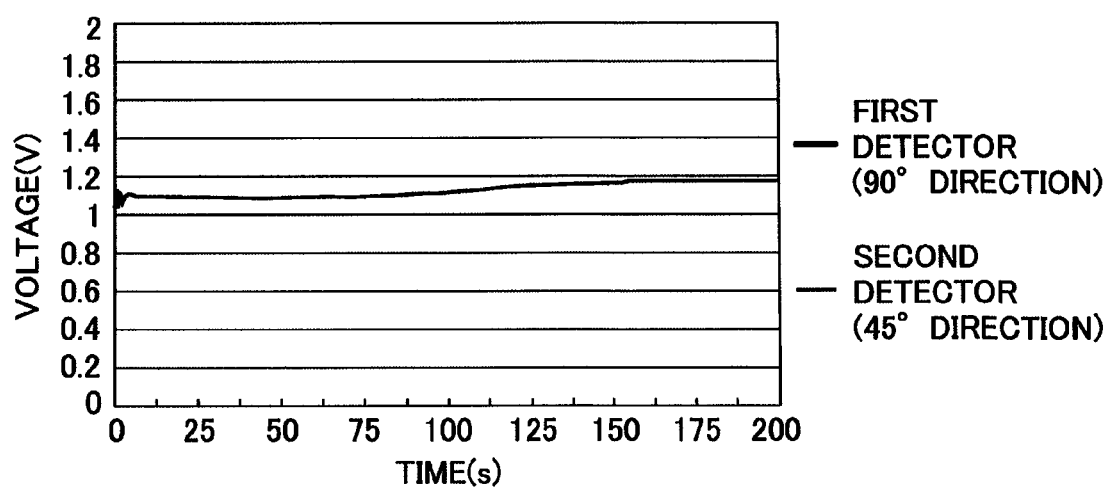

FIG. 4 shows the light intensity variation data acquired in the prothrombin time measurement of a sample obtained by diluting 16-fold the specimen having standard coagulability. FIG. 4 indicates that the signal intensity variation of the first detector 103a is low and the calculation of the blood coagulation time using the signal from the first detector 103a is difficult whereas the signal intensity of the second detector 103b is approximately twice that of the first detector 103a and the calculation of the blood coagulation time using the signal from the second detector 103b is easy.

In this embodiment, the calculation of the blood coagulation time may be conducted by using the signal from the second detector in cases where the calculation of the blood coagulation time using the signal from the first detector of the higher priority order is difficult (when the signal cannot be acquired normally due to blockage of the optical path of the first detector by bubbles, etc. caused by the delivery of the reagent, due to electric noise, etc.) and the signal from the second detector is not being affected by such factors.

Figure 5:
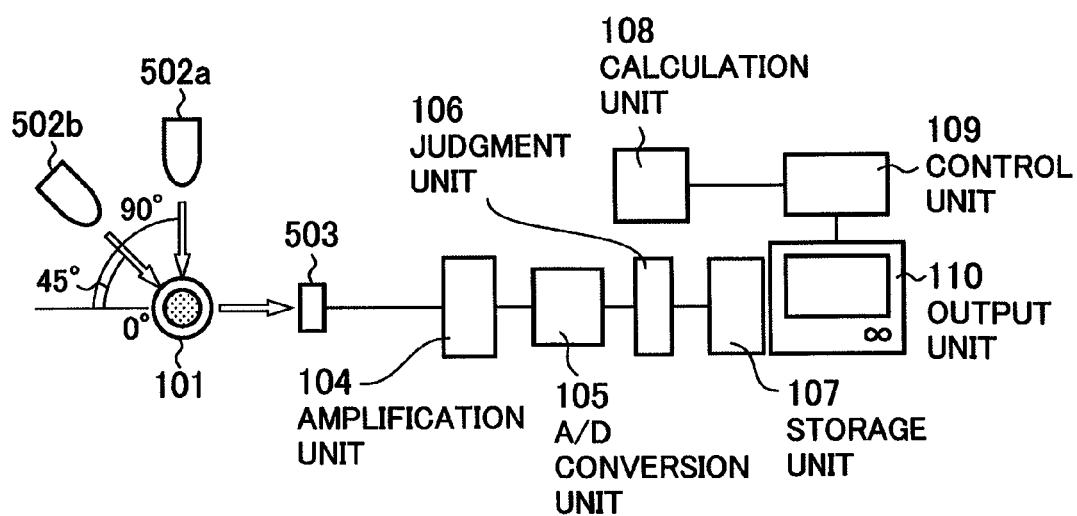
FIG. 5 is a schematic block diagram showing another embodiment of the present invention.

FIG. 5 shows another embodiment of the present invention. A plurality of single-wavelength light sources 502a-502b to which priority orders have previously been assigned are arranged around the reaction container 101. Each single-wavelength light source lights alternately (blinks) at appropriately short blinking intervals (e.g., 100 ms). A single detector 503 is arranged at prescribed angles with respect to these blinking light sources. The liquid mixture of the sample and the reagent is irradiated with the light from the blinking light sources. Scattered light from the liquid mixture is received by the detector 503. In this embodiment, the single-wavelength light sources 502a-502b are arranged on a horizontal plane including the optical axis. A direction of a line connecting the detector 503 and the center of the reaction container 101 is defined as 0°. This means that the forward-scattered light in the 45° direction can be detected by using the scattered light caused by the single-wavelength light source 502b in the 45° direction. Scattered light caused by the alternately blinking single-wavelength light sources 502a-502b is collectively received by the single detector 503. The light received by the detector 503 is transduced into photocurrent, amplified by the amplification unit 104, converted from an analog signal into a digital signal by the A/D conversion unit 105, and stored in the storage unit 107 via the judgment unit 106 as chronological light intensity variation data.

Figure 6:
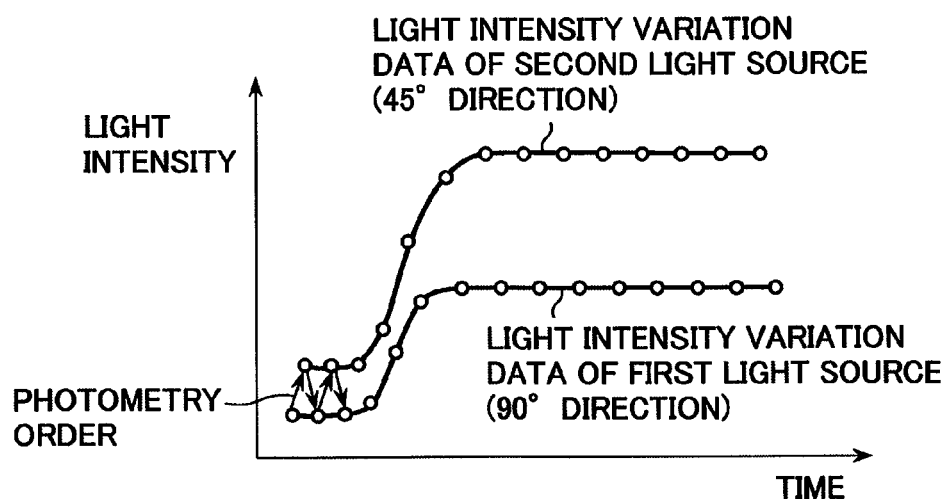
FIG. 6 is a graph showing the outline of the light intensity variation data in an embodiment of the present invention.

FIG. 6 is a graph showing the outline of the light intensity variation data in this embodiment. The stored light intensity variation data is separated by the judgment unit 106 into signals respectively corresponding to the light sources. The judgment unit 106 judges which light intensity variation data (caused by which light source) should be used for the calculation of the blood coagulation time according to a judgment procedure similar to that in the above embodiment. After making the judgment (selection), the judgment unit 106 transmits the selected light intensity variation data to the calculation unit 108. The calculation unit calculates the blood coagulation time from the selected light intensity variation data and transmits the result to the control unit 109. The control unit 109 outputs the result to the output unit 110.

In the embodiments shown in FIGS. 1 and 5, appropriate single-wavelength light sources can be employed by selecting an appropriate wavelength from 320 nm-1000 nm. However, selecting a wavelength within a wavelength range 600 nm-1000 nm is desirable for avoiding the ill effects of the interfering substances like bilirubin and hemoglobin. It is widely known that a shorter light source wavelength causes more scattering of light in cases where the size and number density of the particles to be detected are fixed. Thus, the enhancement of the dynamic range of the signal detection and the improvement of the detectivity can be advanced further by employing a long-wavelength light source and a short-wavelength light source as the single-wavelength light sources 502a and 502b, respectively.

It is also possible to employ a short-wavelength light source and a long-wavelength light source as the single-wavelength light sources 502a and 502b, respectively, to let each light source compensate for the weak point of the other.

It is also possible to employ only one light source in the embodiment shown in FIG. 5 and implement the first and second light sources by executing control to switch the amount of light of the light source at high speed.

While the light source(s) and the detector(s) are arranged horizontally in the embodiments shown in FIGS. 1 and 5, the light source(s) and the detector(s) may also be arranged vertically.

Incidentally, while the above embodiments have been described in regard to blood coagulation analyzers, the analyzers according to the embodiments are applicable also to antigen-antibody reaction analysis such as latex agglutination and immunonephelometry.

DESCRIPTION OF REFERENCE CHARACTERS 101 reaction container
102 single-wavelength light source
103a-103b detector
104 amplification unit
105 A/D conversion unit
106 judgment unit
107 storage unit
108 calculation unit
109 control unit
110 output unit
502a-502b single-wavelength light source
503 detector

The invention claimed is:
1. A blood coagulation analyzer comprising:
 a reaction container in which a sample and a reagent mix and react with each other;

a single-wavelength light source configured to irradiate the reaction container with light;

a plurality of detectors arranged around the reaction container at different angles with respect to an optical axis of the light source that are configured to detect scattered light emitted from the liquid mixture of the sample and the reagent;

an analog to digital converter coupled to the plurality of detectors configured to obtain signals on the basis of the scattered light detected by the plurality of detectors;

a storage unit storing a previously assigned priority with respect to each of the plurality of detectors, and data output from the analog to digital converter including a plurality of chronological light intensity variation data corresponding to each of the plurality of detectors;

a judgment unit coupled to the analog to digital converter and coupled to the storage unit, programmed to:

select light intensity variation data corresponding to one of the plurality of detectors to be used for calculation of a blood coagulation time from the plurality of chronological light intensity variation data corresponding to each of the plurality of detectors stored in the storage unit based on the amount of light intensity variation, determine whether the amount of variation of the light intensity variation data from a detector of a high priority order amongst the plurality of detectors is less than a preset threshold value, and if the amount of variation of the light intensity variation data corresponding to a detector of the high priority order amongst the plurality of detectors is less than the preset threshold value, and select the light intensity variation data corresponding to a detector of a next priority order amongst the plurality of detectors for the calculation of the blood coagulation time; and a calculation unit coupled to the judgment unit, programmed to calculate a blood coagulation time on the basis of the light intensity variation data selected by the judgment unit.

2. The blood coagulation analyzer according to claim 1, wherein the judgment unit is further programmed to select the data corresponding to the detector of the next priority order for the calculation of the blood coagulation time when the light intensity variation data corresponding to the detector of the high priority order is less than the preset threshold value due to a factor affecting the light intensity variation data corresponding to the detector of the high priority order, wherein the factor is at least one of signal noise, partial blockage of an optical path of the detector of the high priority order, and complete blockage of the optical path of the detector of the high priority order.

3. The blood coagulation analyzer according to claim 1, further comprising an amplifier coupled to each of the plurality of detectors and configured to amplify photocurrents transduced from the scattered light detected by the plurality of detectors, wherein the analog to digital converter is coupled to the amplifier and is configured to convert the amplified photocurrents from analog signals into digital signals.

4. A blood coagulation analyzer comprising:

a reaction container in which a liquid mixture of a sample and a reagent react;

a light source which irradiates the reaction container with single-wavelength light;

a plurality of detectors arranged at different angles with respect to an optical axis of the light source, the detectors detecting scattered light emitted from the irradiated reaction container;

an analog to digital converter coupled to the plurality of detectors configured to obtain signals on the basis of the scattered light detected by the plurality of detectors;

a storage unit storing a previously assigned priority order with respect to each of the plurality of detectors and data output from the analog to digital converter including multiple pieces of light intensity variation data corresponding to each of the plurality of detectors;

a judgment unit coupled to the analog to digital converter and coupled to the storage unit, programmed to:

select a piece of light intensity variation data corresponding to one of the plurality of detectors suitable for securing a wide dynamic range and enhance the sensitivity in the blood coagulation analysis from the multiple pieces of light intensity variation data stored in the storage unit based on the amount of light intensity variation, determine whether the amount of variation of the light intensity variation data from a detector of a high priority order amongst the plurality of detectors is less than a preset threshold value, and if the amount of variation of the light intensity variation data from a detector of a high priority order amongst the plurality of detectors is less than a preset threshold value, and select the light intensity variation data corresponding to a detector of a next priority order amongst the plurality of detectors for the calculation of the blood coagulation time; and a calculation unit coupled to the judgment unit, programmed to calculate a blood coagulation time on the basis of the light intensity variation data selected by the judgment unit.

5. The blood coagulation analyzer according to claim 4, wherein the judgment unit is further programmed to select the data corresponding to the detector of the next priority order for the calculation of the blood coagulation time when the light intensity variation data corresponding to the detector of the high priority order is less than the preset threshold value due to a factor affecting the light intensity variation data corresponding to the detector of the high priority order, and wherein the factor is at least one of signal noise, partial blockage of an optical path of the detector of the high priority order, and complete blockage of the optical path of the detector of the high priority order.

6. The blood coagulation analyzer according to claim 4, further comprising:

an amplifier coupled to each of the plurality of detectors and configured to amplify photocurrents transduced from the scattered light detected by the plurality of detectors, wherein the analog to digital converter is coupled to the amplifier and is configured to convert the amplified photocurrents from analog signals into digital signals.

* * * * *